US00PP26892P2

(12) United States Plant Patent
Horvath

(10) Patent No.: US PP26,892 P2
(45) Date of Patent: Jun. 28, 2016

(54) ***ANDROPOGON GERARDII* PLANT NAMED 'DANCING WIND'**

(50) Latin Name: *Andropogon gerardii*
Varietal Denomination: Dancing Wind

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 14/544,422

(22) Filed: Jan. 6, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

(56) References Cited

PUBLICATIONS

Intrinsic Introductions: 2014 Introductions catalog (http://www.intrinsicperennialgardens.com/sitefiles/wp-content/uploads/IPG_Intros_2014-140224.pdf). (3 pages).*

* cited by examiner

*Primary Examiner* — Susan McCormick Ewoldt
*Assistant Examiner* — Karen Redden

(57) ABSTRACT

A new, distinct *Andropogon gerardii* plant as shown and described, characterized by a more upright plant with a height of 140-170 cm, yellow-green colored foliage with red tips and joints, and red fall color that turns scarlet, compared to parent plant.

1 Drawing Sheet

Figure 1:
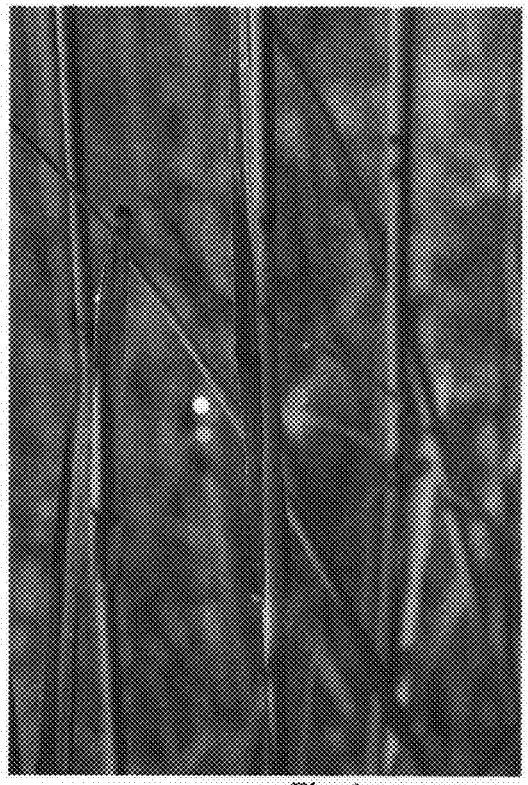

Latin name: *Andropogon gerardii.*
Cultivar name: 'Dancing Wind'.

BACKGROUND OF THE INVENTION

The present invention relates to a new form of *Andropogon gerardii* plant named 'Dancing Wind'. 'Dancing Wind' is a seedling of *Andropogon gerardii* 'Indian Warrior', U.S. Plant Pat. No. 24,999, characterized by a more upright plant with a height of 140-170 cm, yellow-green colored foliage with red tips and joints, and red fall color that turns scarlet, compared to dark green colored foliage and the taller habit of 150-180 cm of the parent plant. The new plant was sown as an open pollinated seed from *Andropogon gerardii* 'Indian Warrior', U.S. Plant Pat. No. 24,999, by the inventor at a wholesale perennial nursery in Hebron, Ill. USA in 2010. The seedling was grown at a nursery in Hebron, Ill. The selection of this plant was due to its more upright growth, shorter height of 140-170 cm, and yellow-green colored foliage with red tips and joints, and red fall color that turns scarlet. Initial asexual reproduction has taken place at a nursery in Hebron, Ill. since 2010, by means of vegetative division. In 2012 we planted 100 plants in 1 gallon pots. To date these plants have remained uniform in height, and foliage color. The new *Andropogon gerardii* has shown to be stable and identical in reproduction to the parent after making over 1200 vegetative divisions from 2011 to 2014.

SUMMARY OF THE INVENTION

In the following description, color references are made to The Royal Horticultural Society Colour Chart (copyright 2001). The new *Andropogon gerardii* plant named 'Dancing Wind' has shown the characteristics of a more upright plant with a height of 140-170 cm, yellow-green colored foliage with red tips and joints, and red fall color that turns scarlet to be unique and stable. For purpose of the comparison the new plant will be referred to as 'Dancing Wind'.

Plants of 'Dancing Wind' can be compared to plants of *Andropogon gerardii* 'Indian Warrior', U.S. Plant Pat. No. 24,999. 1. 'Dancing Wind' has upright growth and a height in the range of 140-170 cm compared to the height of *Andropogon gerardii* 'Indian Warrior' which has an average height of 150-180 cm. 2. 'Dancing Wind' has a foliage color of yellow-green N144 A coloring to 183 D compared to *Andropogon gerardii* 'Indian Warrior' which has foliage color of green 137 A coloring to N77 A.

Plants of 'Dancing Wind' can be also be compared to plants of *Andropogon gerardii* 'Red Bull' not patented. 1. The 'Dancing Wind' has a height in the range of 140-170 cm compared to the height of *Andropogon gerardii* 'Red Bull' which has an average height of 180-210 cm. 2. The new *Andropogon* has a foliage color of yellow-green N144 A coloring to 183 D compared to *Andropogon gerardii* 'Red Bull' which has foliage color that is, close to RHS 136 C. 3. 'Dancing Wind' has a uniform red fall color 183 D and is propagated by division while the *Andropogon gerardii* 'Red Bull' has a variable orange red fall color and is propagated by seed.

DESCRIPTION OF PHOTOGRAPHS

FIG. 1. Shows a two year old plant in August with red tips and joints.

Figure 2:
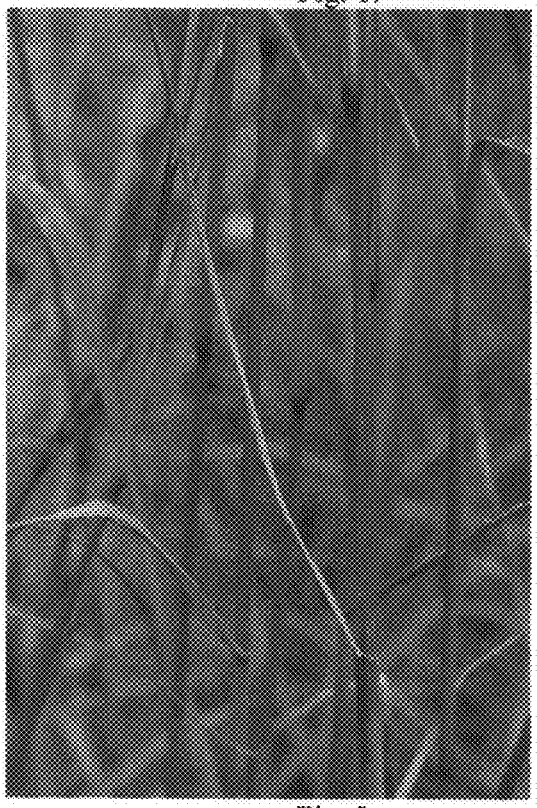

FIG. 2. Shows a two year old plant in September with fall foliage color.

DETAILED BOTANICAL DESCRIPTION

In the following description, color references are made to The Royal Horticultural Society Colour Chart. The plant herein described is an established 3 year old plant growing in a garden, grown in full sun and irrigated in Hebron, Ill. USA. Measurements and numerical values represent averages of typical plants.

Botanical classification: *Andropogon gerardii* cultivar 'Dancing Wind'.

Parentage: *Andropogon gerardii* 'Indian Warrior' seedling.

Propagation: Vegetative division.

Plant description: Overall habit of the new *Andropogon* is clumping with upright culms topped by red colored flowers beginning in August. Vigor is moderate.

*Plant height.*—140-170 cm.

*Plant width.*—60-90 cm.

Foliage and stems:

*Foliage description.*—Glabrous, flat blade, sheathed from node of attachment to ligule, linear.

*Type.*—Deciduous, grass growing in culms.

*Shape.*—Blade.

*Ligules.*—Up to 1 mm long and up to 6 mm wide.

*Number of blades.*—Typically 5 to 6 blades per stem.

*Blade length.*—8 mm wide, up to 46 cm long, ranging from 12 to 44 cm without the sheath.

*Sheath.*—1 cm wide, ranging from 10 to 15 cm long.

*Adaxial leaf description.*—Spring and summer leaf color is 144 A, coloring up to 166 B in fall.

*Abaxial leaf description.*—Spring and summer leaf color is 147 B, coloring up to 165 B in fall.

*Veins.*—Parallel, same color as surrounding leaf on both top and bottom of leaf.

*Culm description.*—Erect, cylindrical, typically with 3 or 4 leaves.

*Culm or stem diameter.*—4 mm average, but typically 4 mm between the nodes and swelling to 5-7 mm at the base of the internodes.

*Number of culms or stems per clump.*—Over 100.

*Node description.*—Cylindrical.

*Number of nodes per culm.*—Average 6.

*Length of internodes.*—Ranges from 10-15 cm.

Flower inflorescence:

*Inflorescence type.*—Terminal raceme with sessile and pedicillate spikelets.

*Rachis.*—1 mm wide and up to 20 cm long, color starts 137 A coloring up to N79A.

*Overall raceme size.*—10 cm wide, 12 cm long.

*Racemes.*—Mostly 3-4 mm wide, 14-15 cm long.

*Rachilla.*—Less than 1 mm wide, 5 mm long, color starts 137A coloring to N79 A.

*Inflorescence color.*—As a whole the color is N79 A.

*Spikelet.*—Sessile and pedicellate — Both 4 mm wide 8 cm long, color is N79 A.

*Individual floret size.*—1 mm wide, 2 cm long including awn.

*Lower glume.*—1-2 mm wide, 12 mm long, color starts 137 A coloring up to N79A.

*Lemma.*—Outer and inner — both, wider than 1 mm less than 2 mm, 12 mm long, color starts 137 A coloring up to N79 A.

*Awn size.*—Is less than 1 mm wide and average 19 mm long.

*Pedicels.*—4 to 5 per, racemes and are shorter toward the base of the plant, 1 mm wide and 5-9 cm long.

*Flower number.*—Approximately 14 florets per racemes, average 45 per spikelet, mature spikelet measuring 5 cm wide, 9 cm long.

*Gynoecium.*—Stigma — 2. color close to N79 A.

*Androecium.*—Anthers — number 3, color — is 19 B.

*Anther size.*—2-4 mm long by 1 mm wide.

*Fertility.*—Fertile with 3 Anthers and 3 Stamens.

*Blooming habit.*—Terminal raceme on stems growing to 155 cm.

*Bloom period and duration.*—Last two weeks of August to the end of September.

*Fruit or seeds.*—Identical to the species except color is darker, color is N79 A, size is 1-2 mm wide, 12 mm long.

*Scent.*—No scent.

*Roots.*—Stiff, fibrous, and freely branching.

Hardiness: United States Department of Agriculture Zones 4-9.

Disease resistance: Plants are not susceptible to any major pests or diseases.

I claim:

1. A new, distinct *Andropogon gerardii* plant as illustrated and described, characterized by a more upright plant with a height of 140-170 cm, yellow-green colored foliage with red tips and joints, and red fall color that turns scarlet, compared to parent plant.

* * * * *